United States Patent
Flaig et al.

(10) Patent No.: US 6,736,266 B2
(45) Date of Patent: May 18, 2004

(54) PACKAGE SYSTEM FOR STORING COSMETIC EFFERVESCENT CLEANSING SACHETS

(75) Inventors: Raymond Michael Flaig, Stamford, CT (US); Natalie Charambura, Fairfield, CT (US); Paul Roland Bergquist, Southport, CT (US); Craig Stephen Slavtcheff, Guilford, CT (US); Matthew Scott Okin, Cresskill, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 84 days.

(21) Appl. No.: 10/225,967

(22) Filed: Aug. 22, 2002

(65) Prior Publication Data

US 2003/0150765 A1 Aug. 14, 2003

Related U.S. Application Data

(60) Provisional application No. 60/355,900, filed on Feb. 11, 2002.

(51) Int. Cl.⁷ ............................................... B65D 73/00
(52) U.S. Cl. ........................ 206/494; 206/525; 206/823; 424/400; 424/404
(58) Field of Search ................................ 206/494, 438, 206/440, 425, 525, 526, 581, 823; 424/400, 404, 464, 466, 484, 43, 44, 47, 78.02

(56) References Cited

U.S. PATENT DOCUMENTS

| | | | |
|---|---|---|---|
| 2,900,258 A | | 9/1959 | Wagner |
| 4,762,230 A | | 8/1988 | Croce |
| 5,050,737 A | * | 9/1991 | Joslyn et al. ............... 206/494 |
| 5,531,325 A | * | 7/1996 | Deflander et al. ........... 206/494 |
| 5,730,311 A | | 3/1998 | Curtis |
| 6,063,390 A | | 5/2000 | Farrell et al. |
| 6,217,854 B1 | | 4/2001 | Farrell et al. |
| 6,294,182 B1 | * | 9/2001 | Znaiden et al. ............. 424/400 |
| 6,364,101 B1 | * | 4/2002 | Schultz ....................... 206/494 |
| 6,451,331 B1 | * | 9/2002 | Slavtcheff et al. .......... 424/404 |
| 6,506,713 B1 | * | 1/2003 | Slavtcheff et al. .......... 424/404 |
| 6,610,311 B2 | * | 8/2003 | Charambura et al. ....... 424/400 |
| 6,610,312 B2 | * | 8/2003 | Farrell et al. ................. 424/43 |
| 2002/0037255 A1 | | 3/2002 | Charambura et al. |

* cited by examiner

*Primary Examiner*—Luan K. Bui
(74) *Attorney, Agent, or Firm*—Milton L. Honig

(57) ABSTRACT

A packaged cosmetic product is provided which includes multiple effervescent sachets placed within a tub with an open dispensing mouth. A carbon dioxide breathable and moisture barrier foil is arranged sealingly to close the dispensing mouth. Any carbon dioxide generated during storage, usually as a result of moisture prematurely effervescing powder within the sachets, is allowed to slowly diffuse into the atmosphere through the window formed by the special foil. The tub is formed of walls which do not have any substantial carbon dioxide breathability but do prevent inward moisture penetration.

12 Claims, 3 Drawing Sheets

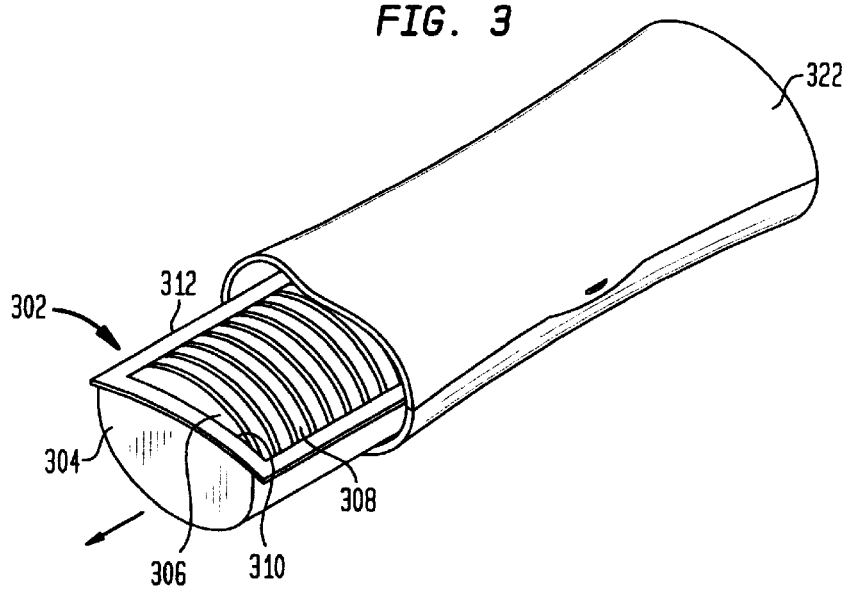
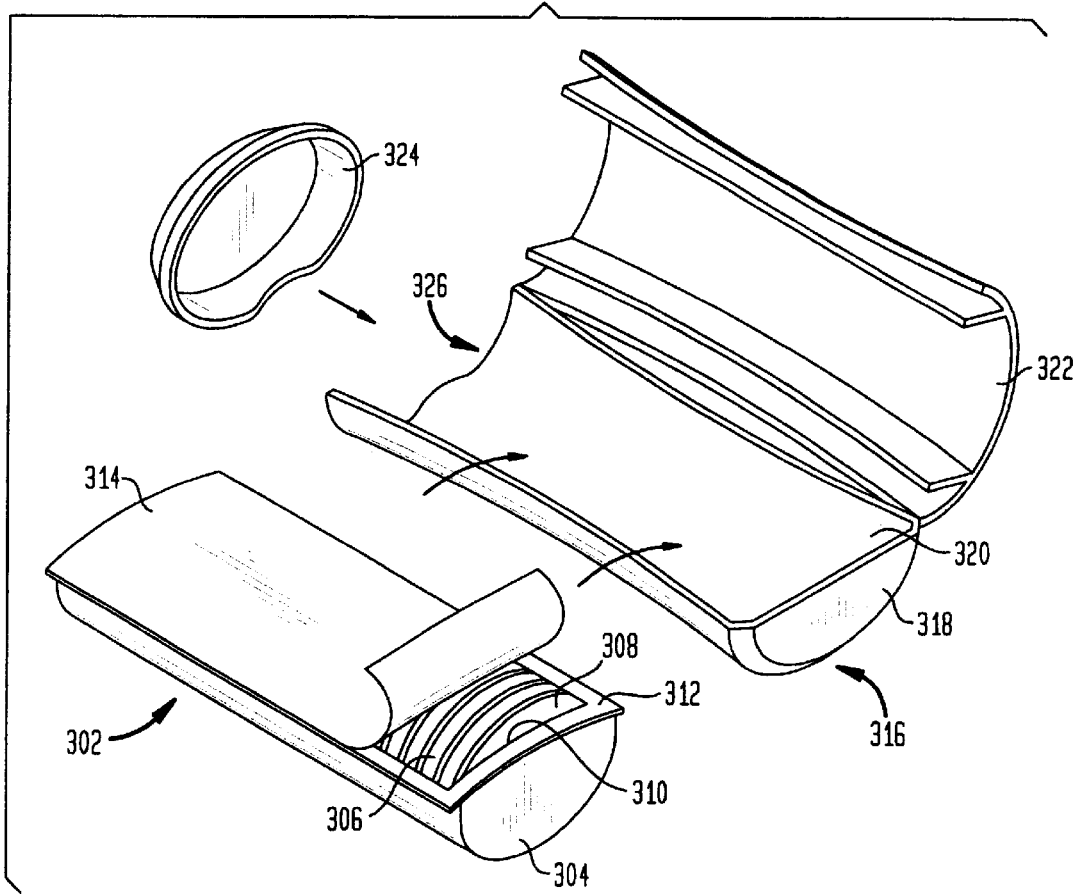

US 6,736,266 B2

PACKAGE SYSTEM FOR STORING COSMETIC EFFERVESCENT CLEANSING SACHETS

CROSS REFERENCES

This application claims the benefit of U.S. Provisional Application Serial No. 60/355,900, filed Feb. 11, 2002.

BACKGROUND OF THE INVENTION

1. Field of the Invention

The invention concerns a packaged cosmetic effervescent cleansing product.

2. The Related Art

Cosmetic products are continuously being sought which differentiate themselves from competitors in some manner. Breakthroughs can arise through a difference in product form. A product form departure has been described in U.S. Pat. No. 6,063,390 (Farrell et al.). A wiping article is therein described which includes an effervescent cleanser composition held within a pouch or sachet formed from a pair of substrate sheets. At least one of those substrate sheets is required to be water permeable. The effervescent composition is a mixture of an acid material such as citric acid and alkaline material such as sodium bicarbonate. Water contact causes the combination to effervesce. Skin benefit agents and a dry surfactant may be formulated within the composition.

Maintenance of product stability is a major challenge with this product form. U.S. Pat. No. 6,063,390 suggests that the wiping article or pillow be packaged within a moisture impermeable outer package such as a laminated foil bag to prevent activation of the effervescent system during storage.

While working with the disclosed system, the present applicants found that outer packaging for moisture penetration prevention aggravated another problem. Adventitious moisture within the formulation, rather than merely seepage from the environment, caused a certain level of effervescence to occur. Carbon dioxide gases were thus generated. The outer packaging intended as a moisture barrier now represented a hindrance to elimination of built up carbon dioxide gases.

It is an object of the present invention to provide an outer package for multiple sachets, each containing an effervescent composition wherein the package not only will prevent moisture from penetrating to the composition but allows for release of any carbon dioxide gases which may be generated during storage.

It is to be noted that the subsequently described invention is broader than the objects or technical problems it is directed to solve.

SUMMARY OF THE INVENTION

A packaged cosmetic product is provided having sachets for cleansing body surfaces, the product including:

- a tub having walls forming a cavity open at one end that serves as a dispensing opening;
- a foil having breathability for carbon dioxide disposed sealingly across the dispensing opening;
- a plurality of sachets filling the tub cavity, each sachet formed of walls, with at least one of the walls being water permeable, each sachet being sealed along all its perimeter; and
- an effervescent cleanser composition being positioned within each of the plurality of sachets.

BRIEF DESCRIPTION OF THE DRAWING

Further objects, features and advantages of the present invention will become more readily apparent through consideration of the following drawing in which:

FIG. 3 is a perspective view of a third embodiment detailing a tub partially inserted into a sturdier vanity case;

FIG. 4 is a perspective view of the third embodiment detailing the tub being inserted into the now fully opened sturdier vanity case.

DETAILED DESCRIPTION OF THE INVENTION

Figure 1:
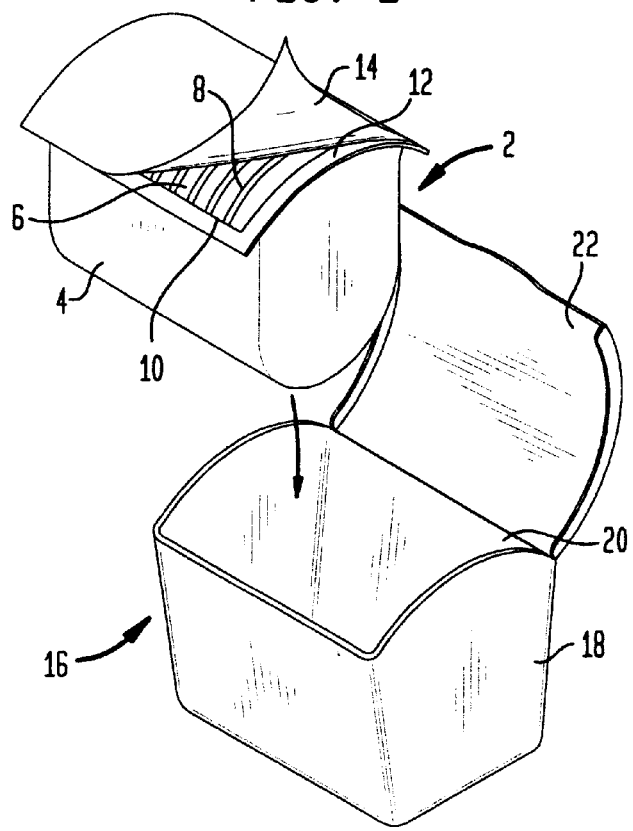
FIG. 1 is a perspective view of a first embodiment detailing a tub being inserted into a sturdier vanity case.

It has been discovered through the present invention that outer packaging for cosmetic effervescent sachets must not only be a barrier protection from water vapor but also must be a breathable material allowing escape of any generated gases, especially carbon dioxide. Thus, the invention provides a seated outer packaging material formed of a foil having breathability.

Furthermore, it has been found important to maximize areas of the outer packaging material for primarily functioning as a moisture barrier. A much smaller area of the outer packaging, indeed a window area, is provided to permit escape of carbon dioxide that may prematurely be effervescing, while simultaneously possessing significant moisture inflow protection properties.

More specifically, there is provided a tub with a cavity for receiving from 2 to about 60, preferably from about 5 to about 30, optimally from about 8 to about 20 effervescent cleanser composition filled sachets. A foil permitting carbon dioxide transmission but not moisture ingression sealingly covers a dispensing mouth of the tub. Only upon first consumer use is the seal broken.

Walls of the tub can be constructed of any single or composite material with proviso that the wall maintains a barrier against moisture seeping into the tub cavity. Suitable materials for wall construction include polyethylene, polypropylene, polyvinylchloride, polyester, polystyrene and mixtures thereof. Multiple layered wall construction may be employed. Particularly preferred for the tub wall material is a co-extruded polystyrene/polyethytene dual layer (ratio about 1:1) material.

Thickness of the tub wall may range from about 0.025 to about 0.8, preferably from about 0.05 to about 0.6, optimally from about 0.08 to about 0.15 centimeters.

Advantageously, the foil may be transparent. The sachet article may thereby be viewable by a consumer through the window of the foil. Aesthetics are likewise thereby improved. Heat seals or adhesives may be employed along edges of the foil to ensure a good seal.

Among preferred materials for the foil are films of polypropylene, polyethylene, polyvinyl chloride and polycarbonate. The materials may be employed as a single layer or as a series of laminated layers. Some of the layers may be formed of a material other than the preferred types, but with proviso that the composite foil meets the requirement for carbon dioxide breathability. An oriented polypropylene co-extruded with a layer of high density polyethylene (containing EVA resin) is the most preferred foil embodiment. Foil thicknesses may range anywhere from about 0.0003 to about 0.03, preferably from about 0.006 to about 0.02, optimally from about 0.01 to about 0.15 centimeters.

Relative ratio of thickness between the tub wall and foil may range from about 1,000:1 to about 2:1, preferably from about 50:1 to about 3:1, more preferably from about 20:1 to about 4:1, optimally from about 10:1 to about 6:1.

The tub is preferably vacuum formed. Besides functioning to prevent moisture penetration, the walls provide rigidity to force multiple sachets to remain in a pre-arranged stacked orientation.

A vanity case may serve as an outer container receiving the tub. Walls of the vanity case may be formed of any plastic or cellulosic material. Thickness of the vanity wall may range from about 0.07 to about 0.7, preferably from about 0.12 to about 0.5, optimally from about 0.2 to about 0.3 centimeters. Relative thickness of the vanity wall to that of the tub may range from about 20:1 to about 1:1, preferably from about 4:1 to about 1.5:1.

A main function of the vanity case is to prevent contaminants from penetrating inside. The vanity case will even in a closed position allow for outward transmission of carbon dioxide along at least some of the closure perimeter.

For purposes of this invention, breathability can be measured by ASTM D3985 intended to measure oxygen permeability but also useful for correlation to carbon dioxide permeability. When operated at 23° C./0% Relative Humidity, carbon dioxide gas permeability should range from about 100 to about 3,000, preferably from about 150 to about 2,000, more preferably from about 200 to about 1500 cc per 645 square cm per 24 hours.

As a consequence of thicker walls or a combination of thicker walls and type of plastic material, the tub will have the disadvantage of much less carbon dioxide breathability but the advantage of greater moisture protection than that of the foil. Indeed, walls of the tub will have a carbon dioxide gas permeability less than about 200, preferably less than about 100, and optimally less than about 75 cc per 645 $cm^2$ per 24 hours.

Another feature of foils suitable for sealing the dispensing opening is a Vapor Transmission Rate for water according to DIN 53122 (measured at 23° C./85% Relative Humidity) which ranges from about 0.001 to about 0.3, preferably from about 0.005 to about 0.1, more preferably from about 0.01 to about 0.1 grams per 645 square cm per 24 hours.

FIG. 1 illustrates a first embodiment of the present invention. A tub 2 is unitarily vacuum formed as walls 4 surrounding a cavity 6. A set of seven effervescent oval sachets 8 are stacked one adjacent the other within the cavity. These sachets are vertically aligned with a major axis of the oval directed upward through a dispensing mouth 10 of the tub.

Along a periphery of the dispensing mouth is a landing 12. A transparent or at least translucent foil 14 covers the dispensing mouth sealingly attached all along the landing 12.

A vanity case 16 serves as an outer containment protecting package. Case 16 includes a receptacle 18 with an opening 20 closeable by a hingedly attached cover 22. The seated sachet containing tub is nested within receptacle 18.

Figure 2:
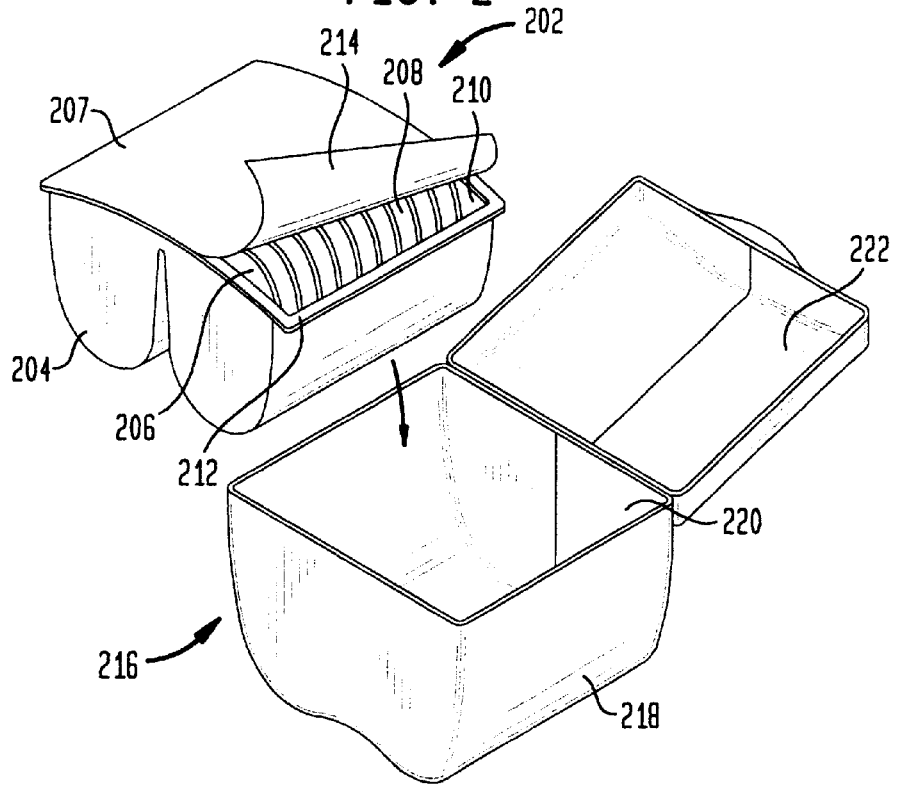
FIG. 2 is a perspective view of a second embodiment detailing a tub partially inserted into a sturdier vanity case.

FIG. 2 illustrates a second embodiment of the present invention. Therein a tub 202 is vacuum formed as an article with unitary walls 204 defining a pair of cavities 206 and 207. Seven effervescent oval sachets are stacked within each of the cavities. The sachets are removable from the tub through a dispensing mouth 210 encompassing both cavities. A landing 212 surrounds a perimeter of the dispensing mouth. A film 214 characterized by breathability for carbon dioxide but low water vapor transmission covers the dispensing mouth and is seated against the landing all along the perimeter.

A vanity case 216 serves as an outer protection within which the tub nests. The vanity case includes an injection molded receptacle 218 characterized by an opening 220 which may be seated from dust contaminants by a hingedly attached cover 222.

FIG. 3 illustrates a third embodiment of the present invention. Therein an injection molded tub 302 forming unitary walls 304 provides a storage cavity 306. Multiple effervescent sachets of oval shape are horizontally stacked within the cavity. A major axis of the oval sachets is oriented in a direction parallel to a plane of dispensing mouth 310. A foil 314 having breathability for carbon dioxide but without transmission of water vapor sealingly covers the dispensing mouth. The foil is thermally bonded against landing 312 to insure tight seat along all of the perimeter of the dispensing mouth.

A vanity case 316 protectively surrounds the tub. FIG. 4 illustrates the vanity case in an open position with the tub separated therefrom. The vanity case has a receptacle 318 with an opening 320. The case is closeable along a horizontal direction by a hingedly connected cover 322 and a separate end cap 324. The cap is useful to cover an end dispensing opening 326 which minimizes exposure of the sachets to moisture in the air.

Figure 5:
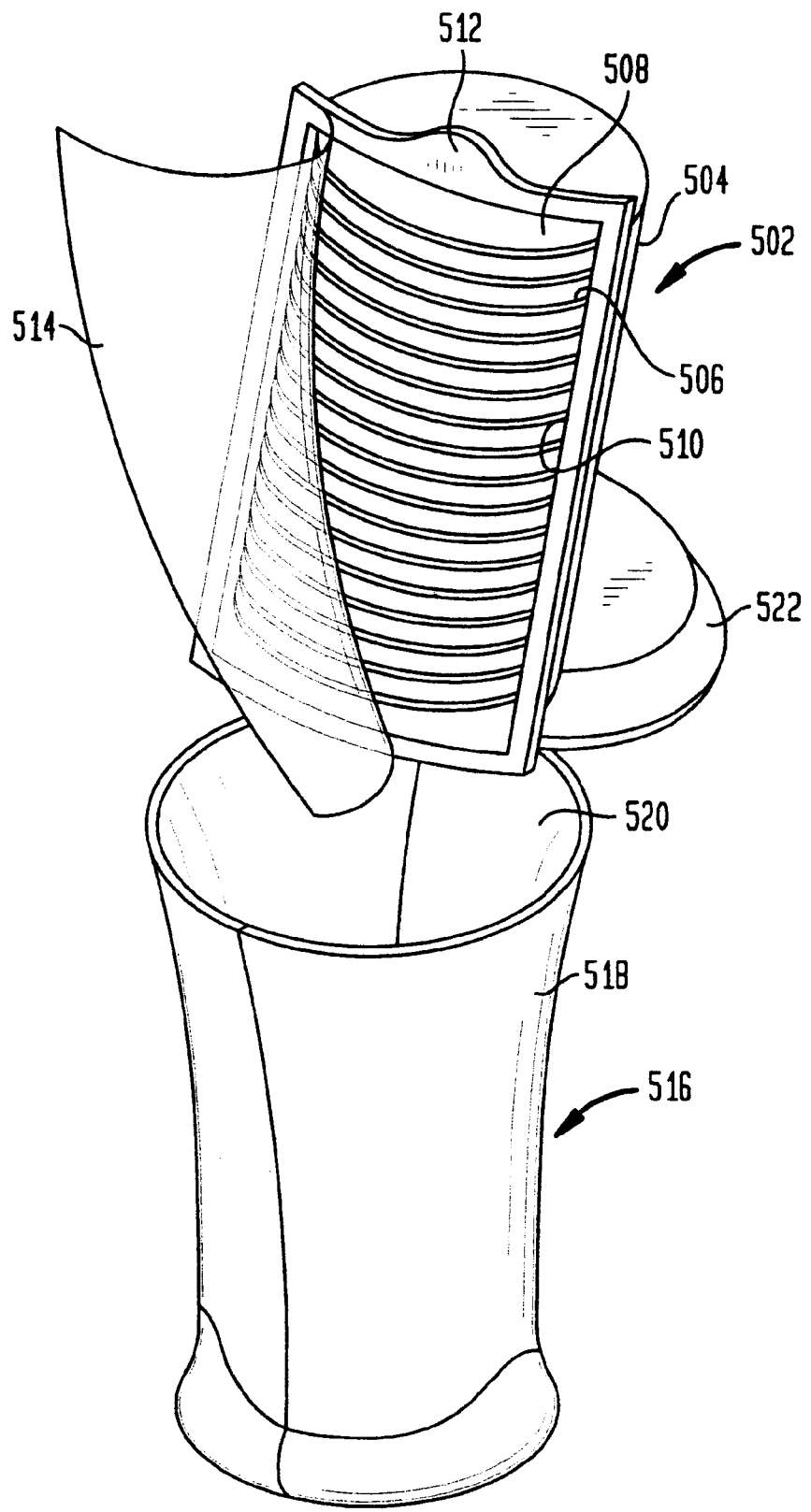
FIG. 5 is a perspective view of a fifth embodiment detailing a tub being inserted into a sturdier vanity case.

FIG. 5 illustrates a fourth embodiment of the present invention. Therein is provided a tub 502. This tub is thermoformed into a structure with walls 504 defining a cavity 506. Multiple effervescent round sachets 508 are stacked within the cavity. The sachets may be dispensed through a dispensing mouth 510. Landing 512 surrounds a perimeter of the dispensing mouth. A foil 514 with breathability for carbon dioxide but not moisture vapor covers the dispensing mouth and is sealed adhesively against the landing.

A vanity case 516 serves as outer dust protective packaging for the tub. The vanity case is extrusion molded as a unitary piece with a receptacle 518 closed at one end and having an opening 520 at an opposite end. The tub nests inside the receptacle and is protected by a cover 522 hingedly attached to opening 520.

In the illustrated embodiments, the tubs are formed from a co-extruded polystyrene/polyethylene laminate with the polyethylene layer appearing on an outer surface of the landing. The foil is an oriented polypropylene with a co-extruded laminate of high density polyethylene admixed with ethylene vinyl acetate as an adhesive/plasticizer. Excellent bonding is achieved between the polyethylene laminate layer of the film and the polyethylene laminate layer of the tub.

Sachets of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

A component of compositions for generating effervescence within the pouch is that of an acidic material. Suitable for this purpose are any acids present in dry solid form. Especially appropriate are $C_2$–$C_{20}$ organic mono- and polycarboxylic acids and especially alpha- and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

Another component for generating the effervescent compositions of this invention within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 10%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

An optional but useful component of the compositions according to the present invention may be that of a surfactant, preferably a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the dry surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, triclocarban, hexetidene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as lipothix 100B® which is a 70:30 mixture of potassium potymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehatose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose.

Most preferred for purposes of this invention are Polymer JR and cationic guar gums such as Jaguar C13S® which is guar hydroxypropyltrimonium chloride. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or botanicals combined may be at levels from abut 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Natural vegetable materials from renewable resources are often desirable in cosmetic compositions. For instance, cosmetic compositions of the present invention may include beta-glucan derived from oats, commercially available under the trademark Microat SF from Nurture Inc., Missoula, Mont.

Colorants may also be included in compositions of the present invention. These substances may range from about 0.05 to about 5%, preferably between 0.1 and 3% by weight.

Effervescent cleansing compositions of this invention will be placed within a pouch formed between a first and second flexible substrate sheet, preferably at least one of these being a flexible sheet. At least one of the sheets must be water permeable, most preferably both sheets should have water permeability. For definitional purposes, first and second sheets can be folded-over panels of a single unitary sheet. Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article. Unlike laundry sachet articles, sachets of the present invention should not rupture to allow dispersion of their granular contents into wash water. Rather it is intended for all cleanser composition components to exit by dissolution through the permeable walls of the pouch.

Skin surfaces against which articles of the present invention are useful include face, body, scalp, axilla and even legs/feet. When the article is a foot cleanser, it would be advantageous for the sachet on one of its sides to be coarse while the second of the sheets may be soft and gentle. An abrasive non-woven flexible sheet in a foot cleanser product is useful for rubbing against calluses while the second sheet of the sachet remains smooth.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition is prepared according to the formulation reported in Table I. Phase A is dry blended in a high speed shearing mixer. Fragrance is then sprayed onto the resultant powder as a Phase B. Three grams of the resultant powder are then placed into a 5 by 8 cm oval sachet formed of non-woven rayon/polyester. All sides are closed by ultrasonic heat sealing. A total of seven sachets are prepared in this manner.

TABLE I

| INGREDIENT | WEIGHT % |
| --- | --- |
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Atginic Acid) | 1.0 |
| Sorbitol | 5.0 |

TABLE I-continued

| INGREDIENT | WEIGHT % |
|---|---|
| PHASE B | |
| Fragrance | 1.0 |

Seven of the resultant sachets are stacked within a tub. A polypropylene foil is then applied across the dispensing mouth of the tub. Heat is applied along edges of the foil to seal it against the landing perimeter of the tub.

EXAMPLE 2

A series of plastic foils were evaluated for breathability allowing escape of carbon dioxide. Carbon dioxide transmission rates were evaluated utilizing ASTM D3985. Test conditions were as follows:

Side 1 of Barrier=760 mm Hg, 100% $CO_2$
Side 2 of Barrier=760 mm Hg, 100% $N_2$
Relative Humidity:
  Side 1 of Barrier=0%
  Side 2 of Barrier=0%

TABLE II

| PLASTIC FILM | MEASURED TRANSMISSION RATE cc (645 cm²/24 hrs.) |
|---|---|
| Polypropylene A | 411 |
| Polypropylene B | 399 |
| Polyethylene A | 1398 |
| Polyethylene B | 1497 |
| Polyethylene Terephthalate (PET) A | 45.3 |
| Polyethylene Terephthalate (PET) B | 42.1 |
| Polyvinylchloride A | 1057 |
| Polyvinylchloride B | 1045 |

Film thickness = 1 mil

Levels below about 100 cc per 645 cm²/24 hrs. insufficiently allow carbon dioxide gas to escape. PET with values no higher than 45.3 as measured and reported in Table II is seen as an unsuitable barrier packaging. By contrast, polypropylene, polyethylene and PVC all exhibited sufficient breathability with values very substantially above the minimum 100.

Water vapor transmission through the foil covering the tub with effervescent cleanser containing sachets should be held to a minimum. Inhibition of water vapor transmission is excellent with polypropylene. Transmission is somewhat higher with PET and PVC.

The foregoing description and examples illustrate selected embodiments of the present invention. In tight thereof variations and modifications will be suggested to one skilled in the art, all of which are within the spirit and purview of this invention.

What is claimed is:

1. A packaged cosmetic product having sachets for cleansing body surfaces, the product comprising:
    a tub having walls forming a cavity open at one end that serves as a dispensing opening;
    a foil having breathability for carbon dioxide disposed sealingly across the dispensing opening, the tub walls having less breathability for carbon dioxide than that of the foil;
    a plurality of sachets filling the tub cavity, each sachet formed of walls, with at least one of the walls being water permeable, each sachet being sealed; and
    an effervescent cleanser composition being positioned within each of the plurality of sachets.

2. The product according to claim 1 wherein the foil comprises polypropylene.

3. The product according to claim 1 wherein the foil and the tub walls are formed of different materials.

4. The product according to claim 1 wherein the tub walls and the foil have a relative thickness ranging from about 1,000:1 to about 2:1.

5. The product according to claim 1 wherein the tub walls and the foil have a relative thickness ranging from about 20:1 to about 4:1.

6. The product according to claim 1 wherein the plurality of sachets numbers from 2 to about 60 per tub.

7. The product according to claim 1 wherein each of the plurality of sachets has an oval shape.

8. The product according to claim 1 wherein the foil is transparent.

9. The product according to claim 1 further comprising a vanity case having a receptacle for receiving the tub, the receptacle further comprising a hingedly connected cover.

10. The product according to claim 9 wherein the vanity case is extrusion molded as a unitary piece.

11. The product according to claim 1 wherein the effervescent cleanser composition is an anhydrous dry solid comprising from about 1 to about 80% of an alkaline material, from about 0.5 to about 80 of an acid material and from about 0.01 to about 30% of a skin benefit agent, each by its concentration being by weight of the composition.

12. A packaged cosmetic product having sachets for cleansing body surfaces, the product comprising:
    a tub having walls forming a cavity open at one end that serves as a dispensing opening;
    a foil having breathability for carbon dioxide disposed sealingly across the dispensing opening, carbon dioxide permeability of the foil ranging from about 100 to about 3,000 cc per 645 cm² per 24 hours measured at 23° C./0% Relative Humidity, the tub walls having less breathability for carbon dioxide than that of the foil;
    a plurality of sachets filling the tub cavity; and
    an effervescent cleanser composition being positioned within each of the plurality of sachets.

* * * * *